United States Patent
Niedospial, Jr. et al.

[19]

[11] Patent Number: 6,156,025
[45] Date of Patent: Dec. 5, 2000

[54] TWIST VALVE

[75] Inventors: John J. Niedospial, Jr., Burlington; Charles Quirico, Warren, both of N.J.

[73] Assignee: Bracco Research USA Inc., Princeton, N.J.

[21] Appl. No.: 09/335,333

[22] Filed: Jun. 17, 1999

[51] Int. Cl.[7] .................................................. A61B 19/00
[52] U.S. Cl. ........................ 604/408; 604/533; 604/905
[58] Field of Search .................................. 604/403, 408, 604/411, 412, 414, 415, 905, 416, 533, 534, 535; 215/247, 249; 206/828, 438; 383/106; 251/149.1

[56] References Cited

U.S. PATENT DOCUMENTS

| | | | |
|---|---|---|---|
| 4,114,617 | 9/1978 | Turner | 128/214 |
| 4,573,974 | 3/1986 | Ondetti | 260/112.5 |
| 4,583,643 | 4/1986 | Sanderson | 206/438 |
| 4,967,941 | 11/1990 | Beck | 222/521 |
| 5,025,829 | 6/1991 | Edwards | 137/512 |
| 5,360,413 | 11/1994 | Leason | 604/30 |
| 5,391,150 | 2/1995 | Richmond | 604/247 |
| 5,573,516 | 11/1996 | Tyner | 604/249 |
| 5,651,776 | 7/1997 | Appling et al. | 604/533 |
| 5,728,087 | 3/1998 | Niedospial | 604/408 |
| 5,738,671 | 4/1998 | Niedospial, Jr. et al. | 604/408 |
| 5,762,646 | 6/1998 | Cotter | 604/410 |
| 5,806,551 | 9/1998 | Meloul et al. | 251/149.1 |
| 5,810,398 | 9/1998 | Matkovich | 604/905 |
| 5,820,614 | 10/1998 | Erskine et al. | 604/533 |
| 5,833,213 | 11/1998 | Ryan | 604/905 |

FOREIGN PATENT DOCUMENTS 0 648 513 A1  4/1995  European Pat. Off. .

*Primary Examiner*—John G. Weiss
*Assistant Examiner*—David J. Cho
*Attorney, Agent, or Firm*—Imre Balogh

[57] ABSTRACT

A twist valve for use in a fluid delivery system is provided for selectively allowing fluid flow and blocking fluid flow therethrough. The twist valve is in communication with a pre-filled flexible container and includes a proximal part and a distal part each having a fluid inlet and a fluid outlet. The proximal and distal parts are equipped with cylindrical helical surfaces which allow them to move toward or away from each other when a twisting force is applied to them. The fluid outlet of the proximal part is blocked with a stopper in the distal part when the twist valve is in the closed position, and is unblocked by the stopper when the twist valve is in the open position.

6 Claims, 7 Drawing Sheets

FIG. 2
FIG. 3
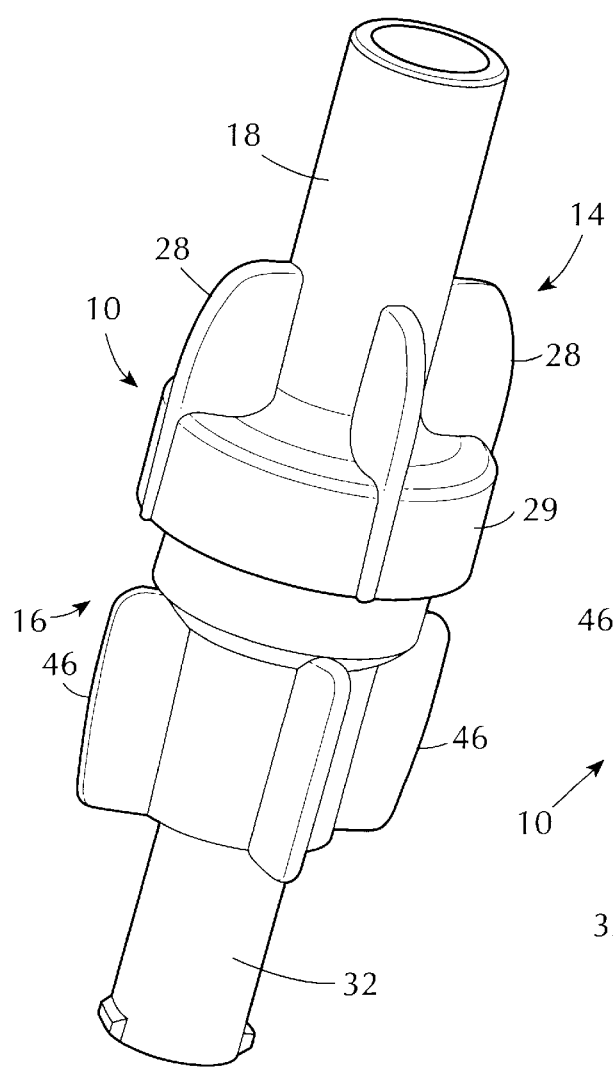
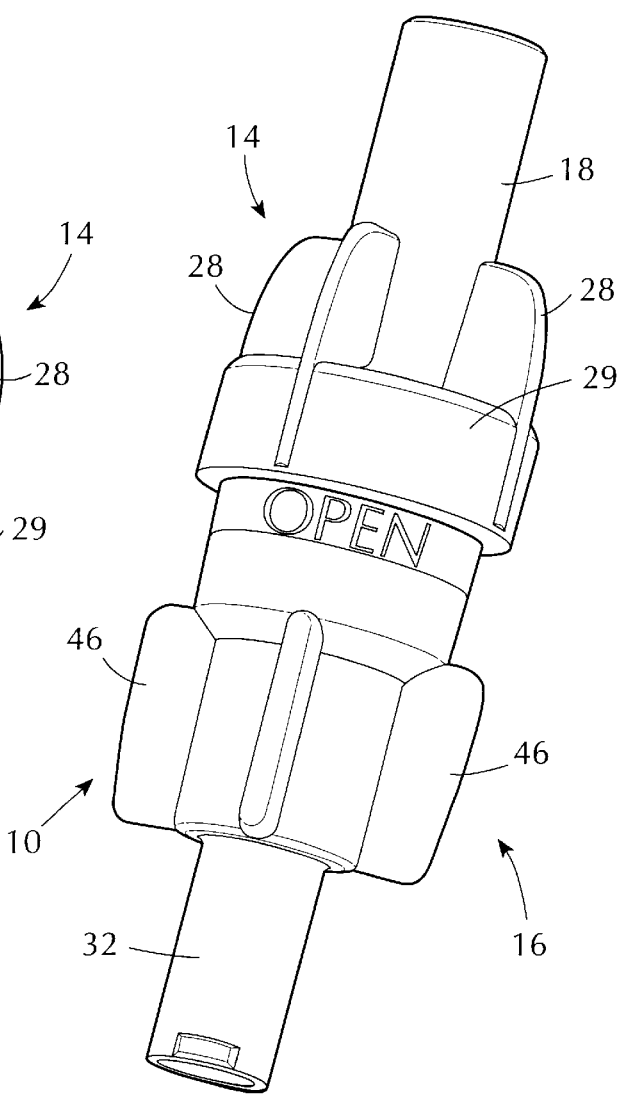

FIG. 4
FIG. 5
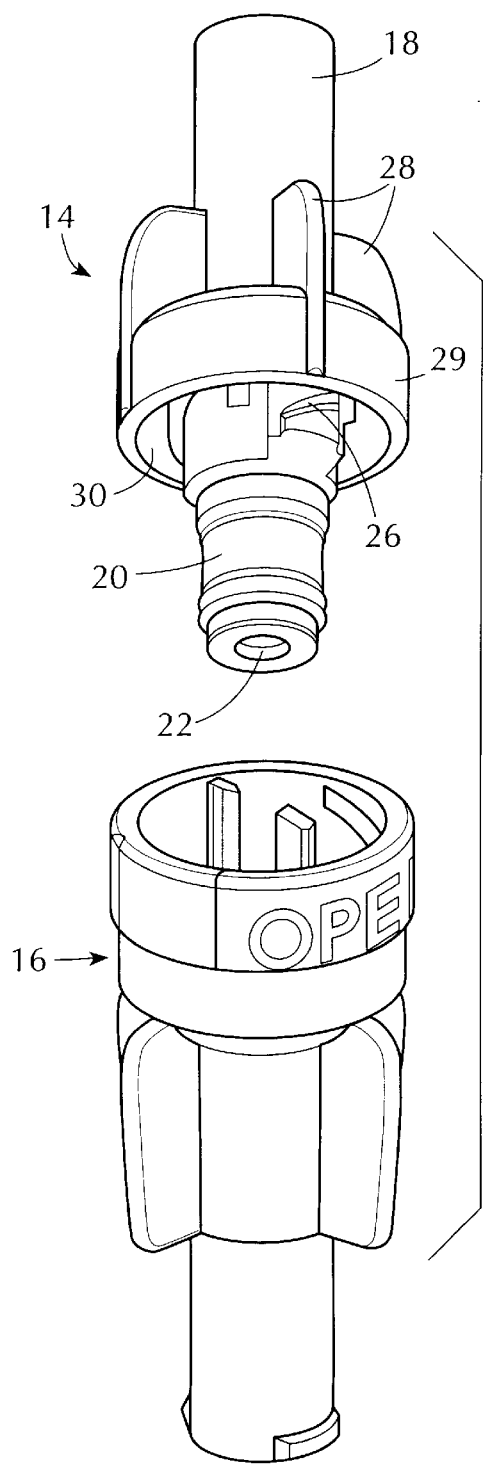
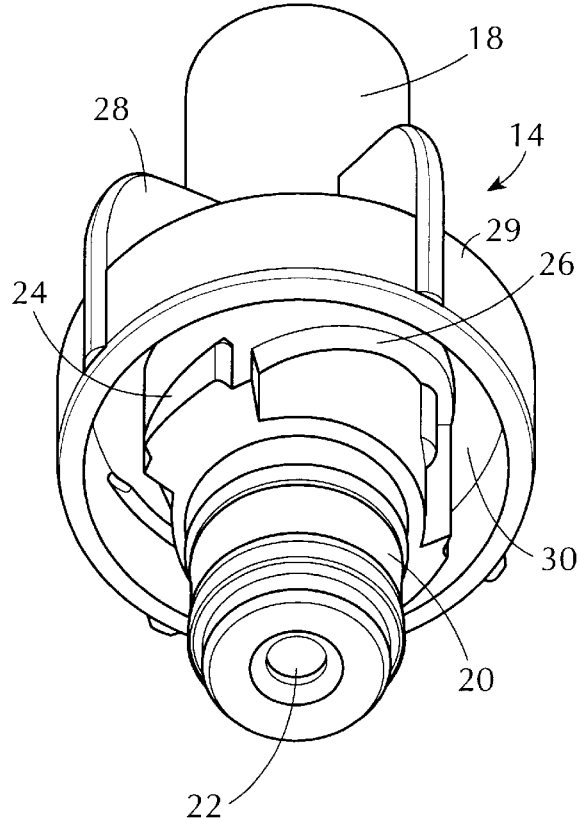

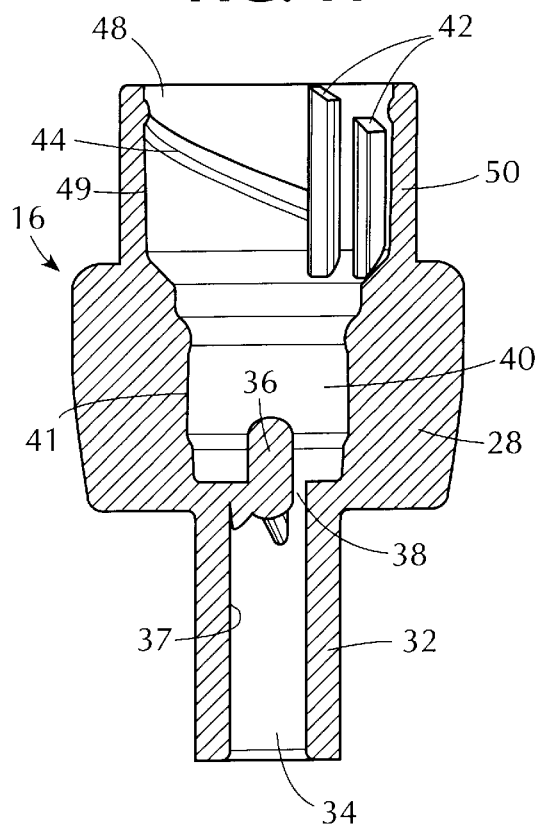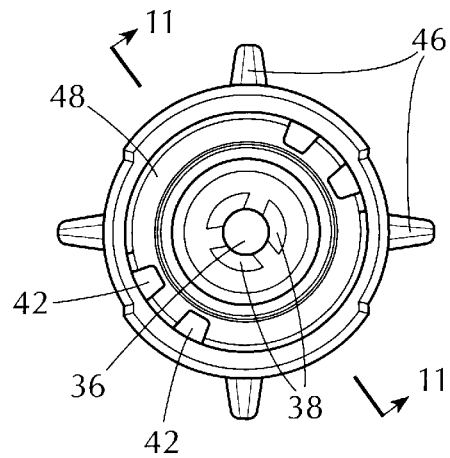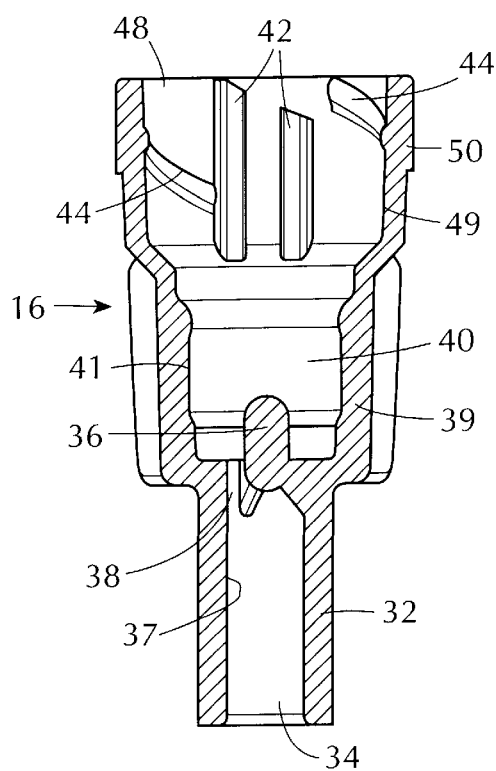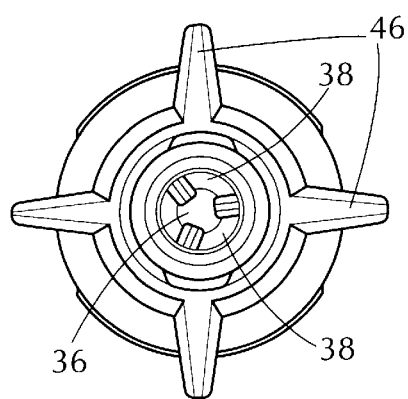

TWIST VALVE

BACKGROUND OF THE INVENTION

1. Field of the Invention

The present invention is directed to a twist valve used in association with a flexible, plastic container, such as a bag, pouch or bottle for the containment and delivery of a parenteral solution, such as diagnostic contrast media, drug formulations and nutrients to a patient in need of such parenteral solutions, wherein the twist valve provides for repeated access to portions or all of the parenteral solutions contained in the flexible container and wherein the flexible container, the parenteral solution, the twist valve and associated access means are autoclavable as a unit.

2. Reported Developments

Flexible medical containers designed for the delivery of parenteral solutions are most often referred to as IV infusion containers embodied in an IV bag containing a fluid to be infused into a patient. An IV line one end of which is integral with, or attached to the bag, and the other end of which is connected to a delivery means, such as a needle, serves to deliver the parenteral solutions to the patient. Typically, the parenteral solution is delivered to the patient by the gravitational force exerted on the IV bag which is elevated above the patient, such as illustrated in U.S. Pat. No. 5,391,150. The parenteral fluid flow is controlled with a valve which includes a resilient valve disc positioned in the parenteral fluid passageway which can be positioned to block the parenteral fluid or to allow the parenteral fluid to flow through the passageway.

Other control means for delivering medical fluids to a patient include force operative check valves such as illustrated in U.S. Pat. Nos. 4,114,617 and 5,025,829. Still other references include the use of resilient discs and resilient conical valve heads constituting part of check valves such as illustrated by U.S. Pat. Nos. 5,391,150 and 5,573,516.

Still another reference, U.S. Pat. No. 5,728,087, discloses a flexible container with multiple access means: a needle access port and spike access port penetrable by a needle or a spike; and an IV access port equipped with a one-way luer slip stopcock.

During administration of IV solutions it is often necessary to shut off the flow of the solutions allowing the medical practitioner to remove only part of the contents while preventing any leakage or spillage. This shut off function may be provided by connecting a pre-sterilized piece of tubing to the IV bag and then, adding a clamp or stopcock to the other end of the tubing. The addition of this implement to a pre-sterilized IV bag just prior to administration is cumbersome requiring aseptic handling of both the IV bag and the implement. The separate sterilization and packaging of the IV bag and the implement add extra cost and extra steps for use of the IV solution.

Alternatively, the IV bag with IV solution therein may be equipped with tubing having a clamp, valve or stopcock thereon, sterilized as a unit and packaged ready for use. However, many drug solutions can only be sterilized using an autoclave, or autoclaving is the preferred method of sterilization. Currently available valves cannot be sterilized by autoclaving without affecting their integrity and subsequent use.

Thus, there is a need for a valve integral with a pre-filled IV bag or other pre-filled flexible, plastic containers which is autoclavable together with the pre-filled IV bag or other pre-filled flexible containers as a unit ready for use in delivering parenteral solutions to the patient.

SUMMARY OF THE INVENTION

In accordance with one aspect of the present invention, there is provided a twist valve for allowing fluid flow and blocking fluid flow therethrough by manually rotating the two parts of the twist valve in relation to each other. The twist valve can be opened and closed as many times as desired, it can be autoclaved without challenging the integrity thereof, and it can also be sterilized by other means such as irradiation.

The twist valve comprises a proximal part and a distal part manufactured separately by methods known in the art, such as injection molding. The two parts then are assembled at the site of manufacture by snapping the parts together. The twist valve is of generally cylindrical configuration having a fluid flow channel inside the cylinder with an inlet port at the proximal end, and an outlet port at the distal end. The term "inlet port" as used herein denotes the port which receives a fluid from a source, such as a pre-filled flexible container, while the term "outlet port" denotes the port through which the fluid is transmitted to a receiving means, such as a tube or luer connector.

Referring now to the present invention in more detail, the proximal part of the twist valve comprises: a generally cylindrical stem having an inside wall and an outside wall, the inside wall defines a channel with an inlet opening on the proximal end thereof and an outlet opening at the distal end thereof, allowing for fluid flow from an outside source through the inlet opening and transmitting fluid flow through the outlet opening.

The outside wall comprises at least one cylindrical helical ramp or ridge serving as thread means to engage a cylindrical helix with which the distal part is equipped; a vertical rib which serves as a tactile stop when the proximal and distal parts are rotated with respect to each other; a cylindrical collar spaced from the cylindrical stem forming a recess over a portion of the stem, the recess in the cylindrical collar is designed to receive a collar on the distal part of the twist valve; and twist wings integral with the cylindrical stem and the cylindrical collar for facilitating handling of the proximal and distal parts when rotated relative to each other.

Preferably, the outside wall of the proximal part comprises two cylindrical helical ramps or ridges and two vertical ribs separating the two helical ramps or ridges. Also, preferably, there are four twist wings provided on the outside wall for ease of handling the twist valve during relative rotation of its two parts.

The distal part of the twist valve comprises: a generally cylindrical stem having a proximal end and a distal end; an inside wall and an outside wall, the inside wall defines a channel having an inlet opening at the proximal end thereof and an outlet opening at the distal end thereof; the inlet opening serves to receive fluid from the proximal part of the twist valve, the fluid travels through the channel and flows out through the outlet opening when the twist valve is in the open position;

the inside wall comprises:
- at least one cylindrical helix to engage the cylindrical helical ramp in the proximal part of the twist valve;
- at least one tactile stop means in the form of a laterally projecting pair of thin ridges serving to control rotation of the proximal and distal parts;
- a plug or stopper projecting toward the proximal end of the channel partially blocking fluid flow through the channel by having at least one opening between it and the inside wall of the channel, the plug being sized to fit into the outlet port in the proximal part of the twist valve to completely close the opening and thereby preventing fluid flow when the twist valve is in the closed position;

the outside wall of the distal part comprises:

an extension collar on the proximal end sized to slideably fit into the recess on the proximal part of the twist valve; and twist wings integral with the cylindrical stem and the extension collar for facilitating handling the helical rotation of the proximal and distal parts relative to each other.

Preferably, the inside wall of the distal part is provided with two cylindrical helixes, and two tactile stop means in the form of two projecting pairs of thin ridges serving to control rotation of the proximal and distal parts. Also preferably, the plug projecting toward the proximal end of the channel is surrounded by three openings between it and the inside wall of the channel.

In use, an external twisting force is exerted respectively on the proximal and distal parts to move them toward each other whereby the plug closes the channel thereby stopping fluid flow through the channel.

Conversely, when an external force is exerted respectively on the proximal and distal parts in moving them away from each other, the plug disengages the exit port in the proximal part of the twist valve thereby opening the channel for fluid flow.

In accordance with another aspect of the present invention, there is provided a twist valve integral with a flexible plastic container, such as a bag, pouch or bottle, for the containment and delivery of parenteral solutions, such as diagnostic contrast media, nutrients and drug formulations to a patient in need of such parenteral solutions.

The flexible plastic container may be of any configuration, such as square, round, oval, hexagonal or octagonal. Preferably, the container is of a generally rectangular configuration comprising:

first and second plastic sheets superimposed and sealed together at their periphery to form a reservoir defining an interior for the containment of a parenteral solution, said reservoir having a top and bottom portion;

an access member, such as tubing, having a proximal end and a distal end, said distal end located at the bottom portion of the reservoir sealed between the two superimposed plastic sheets in the periphery thereof; and the above described twist valve comprising of:

a distal end and a proximal end, for selectively blocking fluid flow therethrough, connected by its proximal end to the distal end of the access member and permanently sealed thereinto, said twist valve serving as a plug when it is in the closed position and allows fluid flow therethrough when it is in the open position.

The twist valve has an outlet connection in the form of a tubing designed to accommodate luer lock syringes or fittings. Alternatively, the outlet of the twist valve may be connected to another tubing by bounding them together, the tubing designed to accommodate the luer lock syringes or fittings.

The so-produced unit can be autoclaved with the reservoir pre-filled with the parenteral solution and the unit packaged ready for use. During the autoclave process, when the twist valve is in the closed position, a water and air-tight bond remains unaffected between the reservoir and the valve and associated tubing. At the point of use the fluid path is opened by twisting the twist valve until a mechanical stop is reached, and closed by twisting the valve in the opposite position. The valve can be opened and closed as many times as desired for accessing the content of the reservoir.

In a modified embodiment, a length of tubing is connected to the outlet of the twist valve and the other end of the tubing is connected to the inlet side of a one-way check valve. The outlet end of the one-way check valve then is connected to a standard luer fitting. The reservoir, the content of the reservoir, the twist valve, one-way check valve and tubings associated with the valves then are autoclaved as one unit and sterile packaged. At the point of use the tubing having the standard luer fitting can be connected to a standard syringe for injecting the content of the reservoir into a patient.

The twist valve of the present invention is preferably configured as an integral part of a pre-filled bag described above, or it can be attached at the point of use to a pre-sterilized pre-filled bag in which case the twist valve and associated tubings and the one-way valve are separately sterilized prior to attachment to the bag containing the parenteral solution.

The design of the twist valve of the present invention provides several benefits: it is low cost since it is made of two parts snap-fit together; the two parts are made of polypropylene or similarly autoclavable material so that they can be sterilized along with various drugs contained in a reservoir which must be autoclaved or of which the preferred sterilization method is autoclaving; the design has a built-in safety factor whereby the total rotation required to seal the fluid path is approximately 15 degrees less than the amount of possible helical rotation; and the twist valve is provided with a tactile stop to the rotation that communicates to the user when the helical rotation is completed.

BRIEF DESCRIPTION OF THE DRAWINGS

FIG. 2 is a perspective view of the twist valve in a closed position;

FIG. 3 is a perspective view of the twist valve in an open position;

FIG. 4 is a perspective view of the twist valve showing the two parts of the twist valve, the proximal part and the distal part, in an exploded view;

FIG. 5 is an enlarged perspective view of the proximal part of the twist valve;

FIG. 10 is a vertical cross-section of the distal part of the twist valve;

FIG. 11 is another vertical cross-section of the distal part of the twist valve taken along the line 11—11 of FIG. 12;

FIG. 12 is a top plan view of the distal part of the twist valve;

FIG. 13 is a bottom plan view of the distal part of the twist valve;

DETAILED DESCRIPTION OF THE INVENTION

Figure 1:
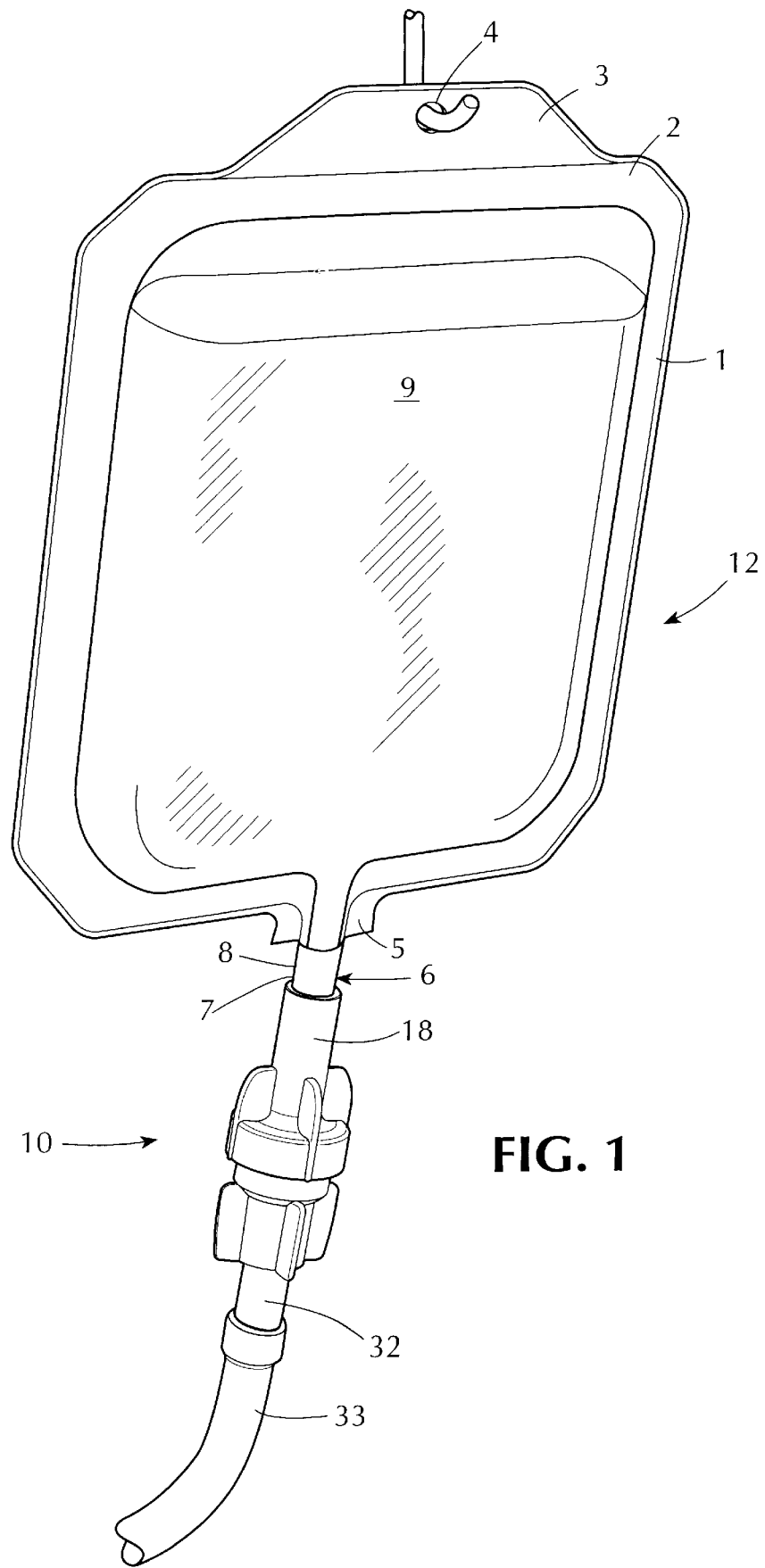
FIG. 1 is a perspective view of the twist valve of the present invention connected to a medical bag containing a fluid therein.

FIG. 1 shows a perspective view of a typical IV bag 12 to which the twist valve 10 is connected. The IV bag is formed by first and second polymeric sheets superimposed and sealed together at their periphery 1, 2, 3 and 5. Periphery 3 at the distal end of the bag is provided with a hole 4 for suspending the IV bag. Periphery 5 encloses an access member such as a flexible tube 6 at the distal end 8 thereof while the proximal end 7 of the flexible tube is closed by twist valve 10 serving as a plug or stopper when it is in the closed configuration and allows IV fluid 9 flow therethrough when it is in an open position.

Twist valve 10 comprises an inlet stem 18 and an outlet stem 32. Inlet stem may be bonded to the proximal end 7 of the access member prior to sterilization of the IV fluid 9 or, alternatively, may be attached to the access member or tube 6 subsequent to the sterilization of the IV bag and its content. In this alternative process the twist valve is sterilized and packaged ready to be connected to the sterilized bag just prior to use.

Outlet stem 32 of the twist valve 10 is equipped with tubing 33 which can accommodate luer lock syringes or other fittings (not shown). Additionally, tubing 33 may be equipped with one-way valves or reflux valves, if so desired, for special purposes such as valves for drip chambers.

The bag may be of various configurations and the fluid contained in the bag may be of various parenteral solutions, such as drugs, contrast media, saline solution and nutritional products.

The twist valve along with tubings and the IV bag containing an IV solution is preferably made of polypropylene so that it can be autoclaved together with these parts as a unit. However, other polymeric materials, such as polystyrene, may be used to construct the twist valve if sterilization, other than autoclaving is used, such as sterilization by irradiation or sterilization using ethylene oxide.

Referring to FIGS. 2 and 3, the twist valve 10 of the present invention comprises two parts fabricated separately and designed to be snapped together under manual or automatically applied pressure: proximal part 14 and distal part 16. The proximal part 14 comprises twist wings 28, and the distal part 16 comprises twist wings 46. As shown in FIGS. 2 and 3, there are a total of four twist wings on each of the two parts for facilitating the twisting of the two parts in closing or opening the twist valve. However, there can be less than four or more than four twist wings on the twist valve if so desired. FIG. 2 shows in perspective view the twist valve 10 in closed position, while FIG. 3 shows in perspective view the twist valve in open position. The proximal and distal parts of the twist valve travel in a path of cylindrical helix when turned respectively to each other. However, the total cylindrical rotation is about 15 degrees less than the complete 360 degrees rotation possible in a helical rotation: the twist valve is equipped with a tactile stop to the rotation that communicates to the user when the helical rotation is completed.

FIG. 4 is a perspective view of the twist valve showing both the proximal part 14, and the distal part 16 thereof in an exploded view, the distal part being illustrated in an open position.

FIG. 5 is an enlarged perspective view of the proximal part 14 of the twist valve showing some of the details thereof in addition to previous parts described in FIGS. 1–4.

Referring to FIGS. 1–5, twist wings 28 are integral with cylindrical collar 29 and inlet stem 18. Inlet stem 18 continues to form main body stem 20 terminating in opening 22. A recess is formed between cylindrical collar 29 and main body stem 20. Inlet stem 18 and main body stem 20 have a smooth flow channel therein to allow flowing of IV fluid 9 from IV bag 12 through opening 22. Main body stem 20 comprises ramp surface 26 and rib 24 which will be referred to as the description of the twist valve continues.

Figure 6:
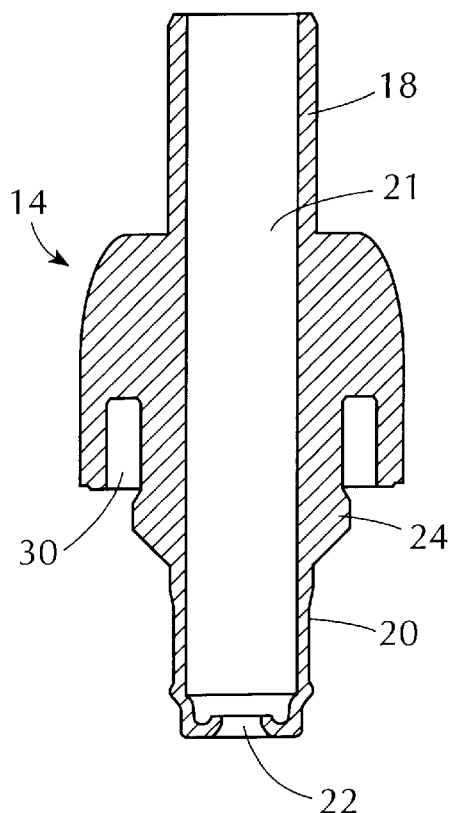
FIG. 6 is a vertical cross-section of the proximal part of the twist valve.

FIG. 6 is a vertical cross-sectional view of the proximal part 14 of the twist valve 10 showing inlet stem 18 and main body stem 20 having flow channel 21 therein terminating in opening 22. Also shown is rib 24 to serve as stopping means for distal part 16 of twist valve 10 when respective twisting of the two parts are effected.

Figure 8:
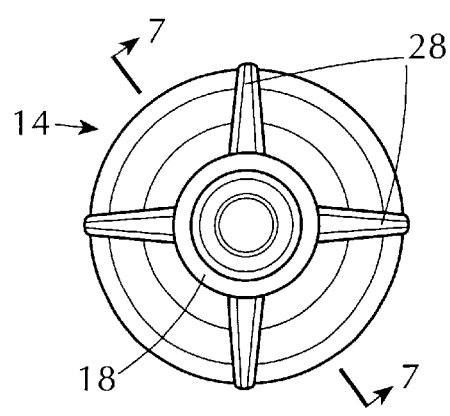
FIG. 8 is a top plan view of the proximal part of the twist valve.

FIG. 8 is a top plan view of the proximal part 14 of the twist valve 10 showing the four twist valve wings 28.

Figure 7:
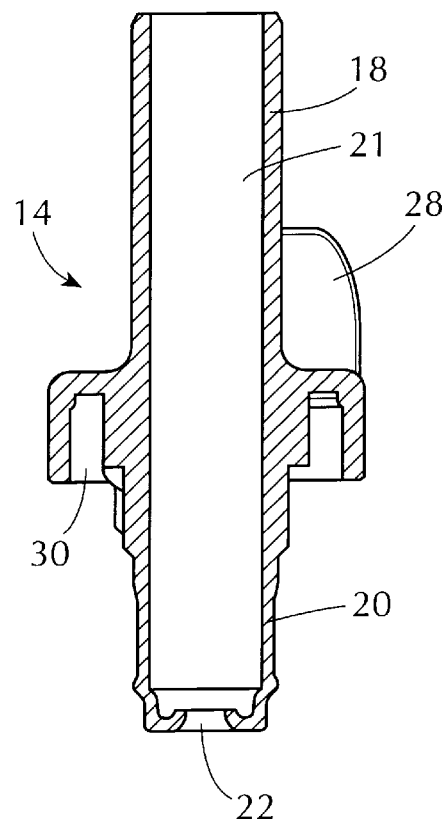
FIG. 7 is another vertical cross-section of the proximal part of the twist valve taken along the line 7—7 of FIG. 8.

FIG. 7 is another cross-sectional view of the proximal part 14 of the twist valve taken along the line 7—7 of FIG. 8 showing essentially the same configuration shown in FIG. 6, except rib 24 is not shown because the proximal part is turned 90° from that shown in FIG. 6. Recess 30 is shown in both FIGS. 6 and 7.

Figure 9:
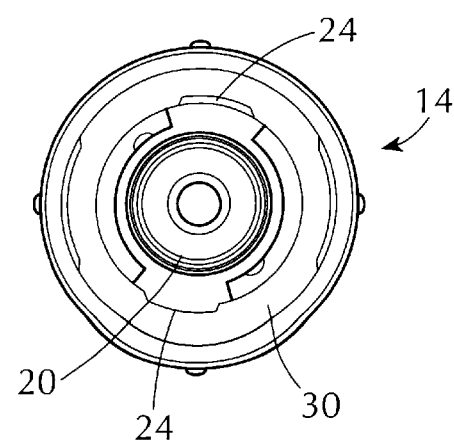
FIG. 9 is a bottom plan view of the proximal part of the twist valve.

FIG. 9 shows, in bottom plan view, the proximal part 14 of the twist valve 10, body stem 20, rib 24 and recess 30.

FIG. 10 is a vertical cross-sectional view of distal part 16 of twist valve 10 comprising:

extension collar 50 at the proximal end which is sized to slidably fit into recess 30 in cylindrical collar of proximal part 14;

outlet stem 32 at the distal end; and main cylindrical body 39 between said extension collar and said outlet stem.

Extension collar 50 having an inside wall 49 is provided with a recess 48. Vertically extending from the inside wall are two tactile stops 42 and cylindrical helixes 44. Main cylindrical body 39 having inside wall 41 encloses recess 40. Extending from the distal portion of inside wall 41 is a plug or stopper 36 adjacent to which there is opening 38. Outlet stem 32 integral with main cylindrical body 39 has inside wall 37 terminating in opening 34. Inside walls 49, 41 and 37 define a channel for fluid flow entering recess 48 and exiting through opening 34.

FIG. 12 is a top plan view of the distal part 16 of twist valve 10 showing plug 36 in the center surrounded by three openings 38. Also shown are four stops 42, recess 48, and four twist wings 46.

FIG. 11 shows a vertical cross-section of distal part 16 taken along line 11—11 of FIG. 12. The view shows parts to those shown in FIG. 10 from a different vantage point of view:

extension collar 50 at the proximal end which is sized to slidably fit into recess 30 in cylindrical collar of proximal part 14;

outlet stem 32 at the distal end; and main cylindrical body 39 between said extension collar and said outlet stem.

Extension collar 50 having an inside wall 49 is provided with a recess 48. Vertically extending from the inside wall are two tactile stops 42 and cylindrical helixes 44. Main cylindrical body having inside wall 41 encloses recess 40. Extending from the distal portion of inside wall 41 is a plug or stopper 36 adjacent to which is opening 38. Outlet stem 32 integral with main cylindrical body 39 extends therefrom and has inside wall 37 terminating in opening 34. Inside walls 49, 41 and 37 define a channel for fluid flow entering recess 48 and exiting through opening 34.

FIG. 13 is a bottom plan view of distal part 16 showing: plug or stopper 36; openings 38 around the plug or stopper and twist wings 46.

Figure 14:
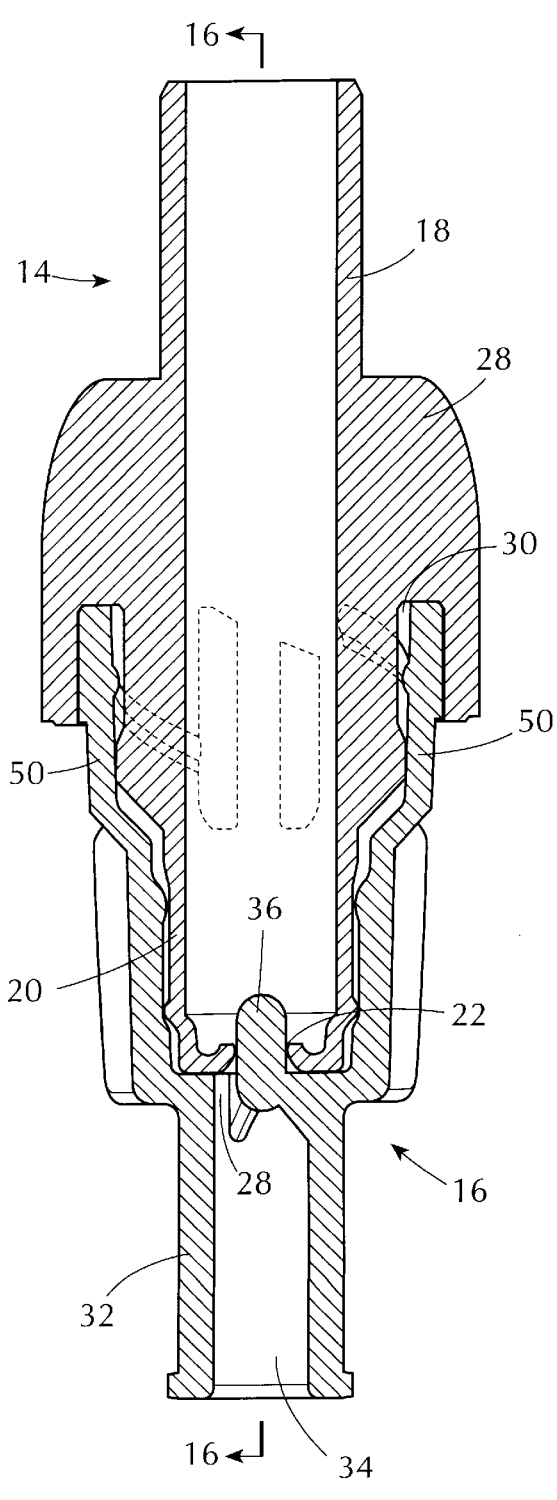
FIG. 14 is a cross-section of the proximal and distal parts of the twist valve in closed position.

FIG. 14 is the cross-section of the proximal part 14 and the distal part 16, snapped together to form twist valve 10 which is shown in the closed position. Extension collar 50 is inserted in recess 30; plug 36 of the distal part 16 closes opening 22 in proximal part 14.

Figure 16:
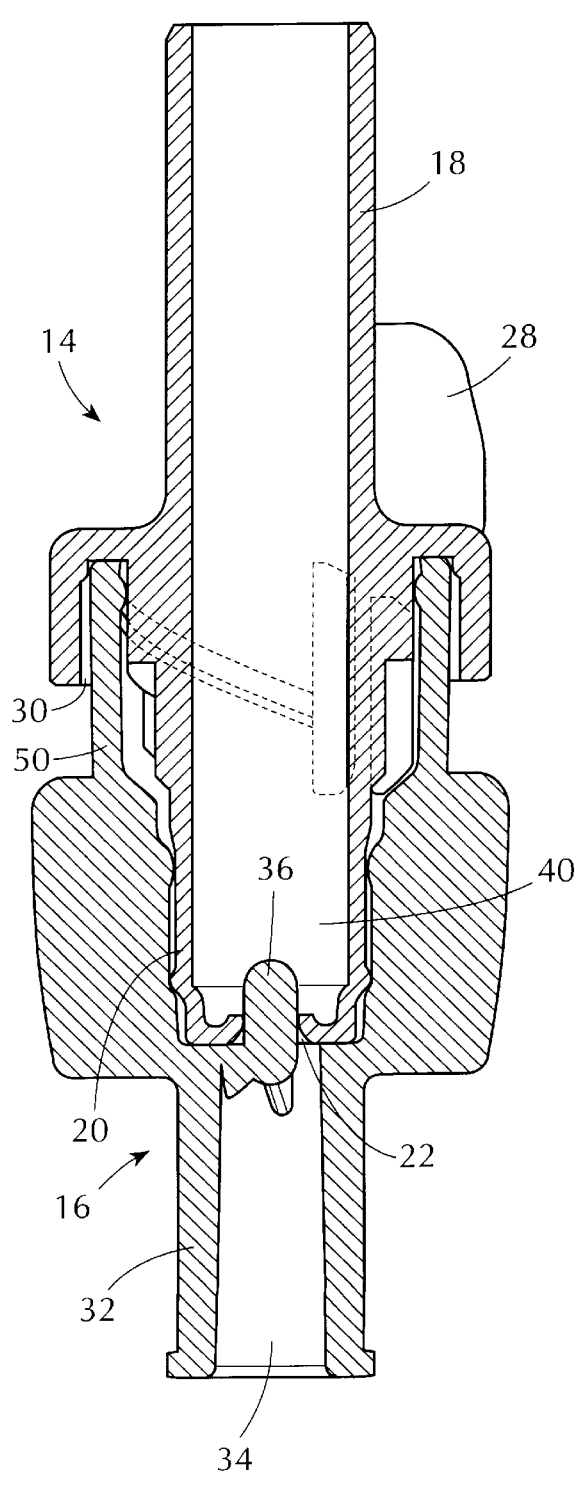
FIG. 16 is a cross-section of the proximal and distal parts of the twist valve in closed position taken along the line 16—16 of FIG. 14.

FIG. 16 is a cross-section of the proximal part 14 and distal part 16 of the twist valve 10 in closed position taken along the line 16—16 of FIG. 14. Collar extension 50 occupies recess 30 and plug 36 closes opening 22 preventing outflow of a fluid through outlet opening 34.

Figure 15:
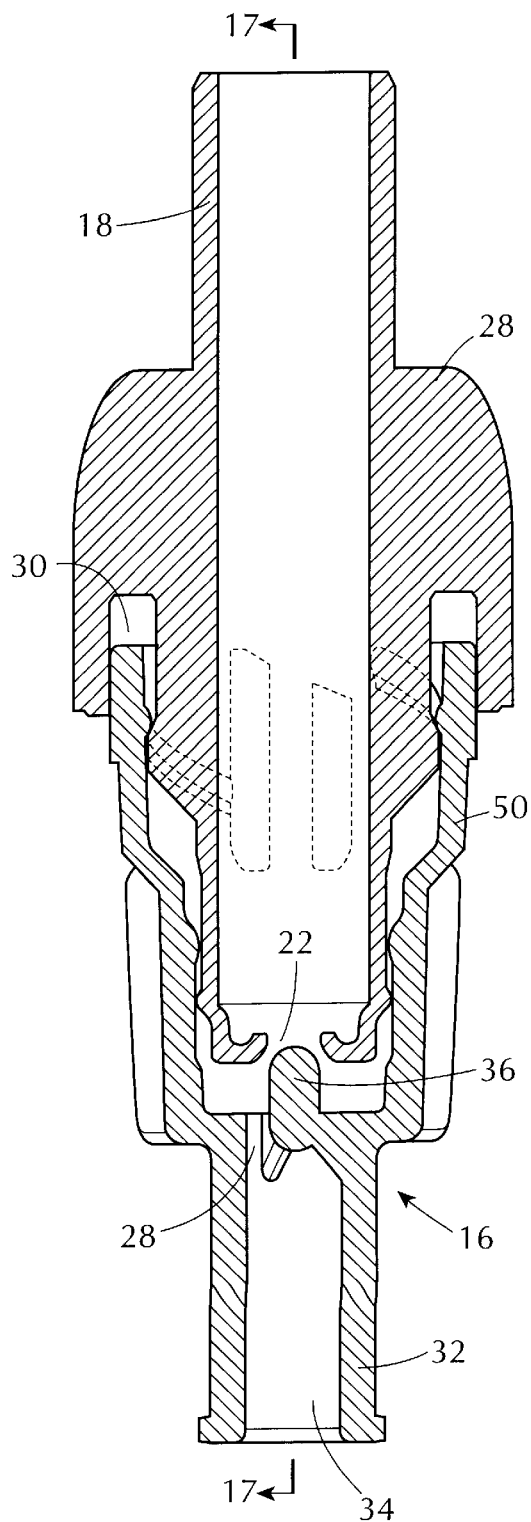
FIG. 15 is a cross-section of the proximal and distal parts of the twist valve in open position.

FIG. 15 is the cross-section of the proximal part 14 and the distal part 16, snapped together to form twist valve 10 which is shown in the open position. Extension collar 50 only partially occupies recess 30 in proximal part 14 and plug 36 does not close opening 22 thereby allowing fluid flow into channel 41 and through outlet opening 34.

Figure 17:
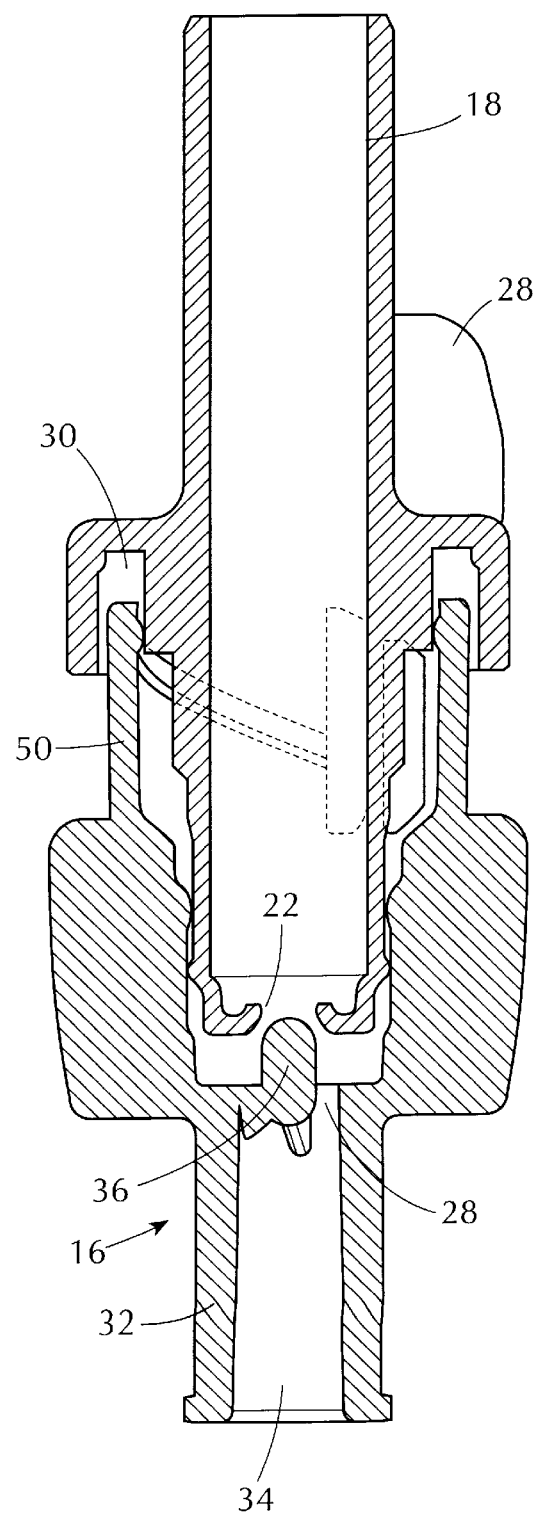
FIG. 17 is a cross-section of the proximal and distal parts of the twist valve in open position taken along the line 17—17 of FIG. 15.

FIG. 17 is a cross-section of the proximal part 14 and the distal part 16 of the twist valve 10 in open position taken along the line 17—17 of FIG. 15.

Extension collar 50 only partially occupies recess 30 in proximal part 14, and plug 36 does not close opening 22 thereby allowing fluid flow through outlet opening 34.

The opening and closing of the twist valve is accomplished by a twisting motion which raises or lowers plug 36 to engage or disengage opening 22. The relative movement of proximal part 14 and distal part 16 is enabled by ramp 26 in the proximal part which twistably engages cylindrical helix 44 in the distal part. Stops 42 in distal part and ribs 24 in the proximal part control the extent of travel of proximal part into and out of distal part 16.

| PARTS LIST | |
| --- | --- |
| Sealed Periphery of IV bag | 1, 2, 3 and 5 |
| Hole in periphery 3 | 4 |
| Access member or tube | 6 |
| Proximal end of access member or tube | 7 |
| Distal end of access member or tube | 8 |
| IV fluid | 9 |
| Twist valve | 10 |
| IV bag | 12 |
| Proximal part of twist valve | 14 |
| Distal part of twist valve | 16 |
| Inlet stem on twist valve | 18 |
| Main body or outlet stem of proximal part | 20 |
| Flow channel | 21 |
| Opening in main body stem | 22 |
| Rib on main body stem | 24 |
| Ramp surface in main body stem | 26 |
| Twist wings on proximal part | 28 |
| Cylindrical collar on proximal part | 29 |
| Recess in cylindrical collar of proximal part | 30 |
| Outlet stem on twist valve | 31 |
| Stem of distal part (outlet stem) | 32 |
| Tube connected to outlet stem | 33 |
| Outlet or opening in distal part | 34 |
| Plug or stopper in distal part | 36 |
| Inside wall of main cylindrical body | 37 |

-continued

| PARTS LIST | |
| --- | --- |
| Openings adjacent to plug | 38 |
| Main cylindrical body in distal part | 39 |
| Recess in main cylindrical body in distal part | 40 |
| Inside wall of main cylindrical body | 41 |
| Stops in distal main body | 42 |
| Cylindrical helix in distal part | 44 |
| Twist wings on distal part | 46 |
| Recess in extension collar | 48 |
| Inside wall of extension collar | 49 |
| Extension collar | 50 |

Various modifications of the present invention will become apparent to those skilled in the art. The invention is intended to include such modifications to be limited only by the scope of the claims.

What is claimed is:

1. A twist valve-flexible container assembly, said flexible container having a parenteral solution therein comprising:

first and second plastic sheets superimposed and sealed together at their periphery to form a reservoir defining an interior for the containment of said parenteral solution, said reservoir having a top and bottom portion;

an access member having a proximal end and a distal end, said distal end located at the bottom portion of the reservoir sealed between the two superimposed plastic sheets in the periphery thereof; and a twist valve having a distal part and a proximal part, for selectively blocking fluid flow therethrough, connected by its proximal part to the distal end of the access member and permanently sealed thereinto, said twist valve serving as a plug when it is in the closed position and allows fluid flow therethrough when it is in the open position, said proximal part comprises:
a) a generally cylindrical stem having an inside wall and an outside wall, said inside wall defining a channel, said channel having an inlet opening at the proximal end thereof and an outlet opening at the distal end thereof allowing fluid flow through said channel and through said inlet opening and outlet opening;
b) a cylindrical helical ramp on said outside wall;
c) a vertical rib on said outside wall serving as a tactile stop when said distal part snapped on said proximal part and travels on the cylindrical helical ramp;
d) a cylindrical collar spaced from said cylindrical stem forming a recess over a portion of said cylindrical stem; and
e) twist wings integral with said cylindrical stem and said cylindrical collar for facilitating helical rotation of said proximal part and said distal part relative to each other;

said distal part comprises:
f) a generally cylindrical stem having a proximal end and a distal end, an inside wall and outside wall, said inside wall defining a channel, said channel having an inlet opening at the proximal end thereof and an outlet opening at the distal end thereof allowing fluid flow through said channel and through said inlet opening and outlet opening;

said inside wall comprises:
g) a cylindrical helical surface to engage said cylindrical helical ramp on the outside wall of said proximal part, and a tactile stop serving as a control during rotation of said proximal part and said distal part; and h) a plug projecting from the inside wall sized to close the outlet opening in said proximal part;

said outside wall comprises:

i) extension collar on the proximal end of said distal part to slidably fit into said recess in said proximal part; and j) twist wings integral with said cylindrical stem and said extension collar for facilitating helical rotation of said proximal part and said distal part relative to each other;

whereby when an external twisting force is respectively exerted on said proximal part and on said distal part in moving them toward each other, said plug closes the exit port in said proximal part thereby stopping fluid flow through said channel; and when an external twisting force is respectively exerted on said proximal part and on said distal part in moving them away from each other, said plug disengages said exit port in said proximal part thereby opening said fluid flow channel for passage of fluid therethrough.

2. The twist valve-flexible container assembly of claim 1 made of polypropylene.

3. The twist valve-flexible container assembly of claim 1 made of polystyrene.

4. The twist valve-flexible container assembly of claim 1 sterilized by autoclave.

5. The twist valve-flexible container assembly of claim 1 sterilized by ethylene oxide.

6. The twist valve-flexible container assembly of claim 1 sterilized by irradiation.

* * * * *